United States Patent [19]
Harandi et al.

[11] Patent Number: 4,950,823
[45] Date of Patent: Aug. 21, 1990

[54] BENZENE UPGRADING REFORMER INTEGRATION

[75] Inventors: Mohsen N. Harandi, Lawrenceville; Hartley Owen, Belle Mead, both of N.J.

[73] Assignee: Mobil Oil Corp., New York, N.Y.

[21] Appl. No.: 375,172

[22] Filed: Jul. 3, 1989

[51] Int. Cl.$^5$ .............................................. C07C 2/12
[52] U.S. Cl. ................................... 585/322; 585/323; 585/411; 585/422; 585/424; 585/446; 585/467; 585/880; 585/807; 203/DIG. 9
[58] Field of Search ............... 585/319, 322, 323, 324, 585/329, 330, 407, 807, 809, 411, 422, 424, 446, 533, 800, 317, 467; 203/DIG. 9, 73, 88

[56] References Cited

U.S. PATENT DOCUMENTS

| | | | |
|---|---|---|---|
| 3,537,981 | 11/1970 | Parker | 585/807 |
| 3,625,879 | 12/1971 | Horne et al. | 208/68 |
| 3,729,409 | 4/1989 | Chen | 208/135 |
| 3,751,506 | 8/1973 | Burress | 260/671 |
| 3,862,254 | 1/1975 | Eisenlohr et al. | 585/807 |
| 4,016,218 | 4/1977 | Haag et al. | 260/671 |
| 4,115,471 | 9/1978 | Kesler | 203/88 |
| 4,150,062 | 4/1979 | Garwood et al. | 260/673 |
| 4,209,383 | 6/1980 | Herout et al. | 208/93 |
| 4,532,041 | 7/1985 | Shuey et al. | 585/818 |
| 4,749,820 | 6/1988 | Kuo et al. | 585/319 |

Primary Examiner—Anthony McFarlane
Attorney, Agent, or Firm—Alexander J. McKillop; Charles J. Speciale; L. G. Wise

[57] ABSTRACT

A process and apparatus are disclosed for the production of gasoline from a $C_4^-$ fuel gas containing ethene and propene and catalytic reformate containing $C_6$ to $C_8$ aromatics. The $C_4^-$ fuel gas is contacted with debutanized catalytic reformate over a zeolite catalyst under process conditions to convert ethene and propene in the $C_4^-$ fuel gas to $C_5^+$ aliphatic and aromatic hydrocarbon gasoline and to convert $C_6$ to $C_8$ aromatics in the reformate to $C_7$ to $C_{11}$ aromatic hydrocarbon gasoline. Reformer fractionation system containing debutanizer column and separator stabilizes effluent gasoline and recycles unconverted light aromatics.

22 Claims, 2 Drawing Sheets

BENZENE UPGRADING REFORMER INTEGRATION

FIELD OF THE INVENTION

The present invention relates to a petroleum refining process for the production of gasoline product. The present invention more specifically relates to the production of gasoline by contacting a $C_4-$ fuel gas containing ethene and propene with a catalytic reformate containing $C_6$ to $C_8$ aromatics over a zeolite catalyst to convert the fuel gas to $C_5+$ hydrocarbon gasoline and to convert the $C_6$ to $C_8$ aromatics to lower alkyl aromatic hydrocarbon gasoline. The process of the present invention provides for the integration of a reforming operation and an olefins oligomerization operation by employing a single product recovery system. The process includes the catalytic reforming of naphtha to obtain the catalytic reformate feed and the fluid catalytic cracking of hydrocarbons to obtain the $C_4-$ fuel gas feed to the zeolite catalyst conversion zone.

BACKGROUND OF THE INVENTION

The fluid catalytic cracking of hydrocarbons in modern refinery operations produces large amounts of $C_4-$ fuel gas of little or no gasoline product value and the catalytic reforming of hydrocarbons produces large amounts of $C_6$ aromatic hydrocarbon which though having value as gasoline blending stock is produced in excessive amounts.

The present invention particularly relates to a catalytic technique for upgrading light olefin gas to heavier hydrocarbons and to alkylating $C_6$ to $C_8$ aromatics to higher octane heavier lower alkyl aromatic hydrocarbons. It provides a continuous process for processing olefinic light gas feedstock, containing ethene and propene, or other lower alkenes, to produce $C_5+$ hydrocarbons, such as olefinic liquid fuels, isobutane, aromatics, e.g. benzene, and other useful products and at the same time alkylating $C_6$ to $C_8$ aromatics to produce $C_1$ to $C_4$ lower alkyl substituted aromatic hydrocarbons for use as gasoline blending stock. Ethene (ethylene, $C_2H_4$)-containing gases, such as petroleum cracking offgas, and catalytic reformate containing benzene, toluene, xylene and ethyl benzene are useful feedstocks for the process.

In particular, the present process provides a single product recovery system for two separate conversion reactions, a reforming reaction and an olefins oligomerization-alkylation reaction.

Developments in zeolite catalysis and hydrocarbon conversion processes have created interest in utilizing olefinic feedstocks for producing $C_5+$ gasoline, diesel fuel, etc. In addition to basic chemical reactions promoted by ZSM-5 type zeolite catalysts, a number of discoveries have contributed to the development of new industrial processes. These are safe, environmentally acceptable processes for utilizing feedstocks that contain lower olefins, especially $C_2-C_4$ alkenes and feedstocks containing aromatic compounds, especially $C_6$ to $C_8$ aromatics.

U.S. Pat. No. 3,729,409 (Chen) discloses improving the yield-octane number of a reformate by contacting the reformate in the presence of hydrogen over a zeolite catalyst. U.S. Pat. No. 4,150,062 (Garwood et al) discloses a process for the conversion of $C_2$ to $C_4$ olefins to produce gasoline which comprises contacting the olefins with water over a zeolite catalyst. U.S. Pat. No. 4,016,218 (Haag et al) and U.S. Pat. No. 3,751,506 (Burress) disclose processes for the alkylation of benzene with olefins over a ZSM-5 type catalyst. U.S. Pat. No. 4,209,383 (HeRoute et al) discloses the catalytic alkylation of benzene in reformate with $C_3-C_4$ olefins to produce gasoline.

U.S. patent application Ser. No. 157,831, filed Feb. 19, 1988, relates to a process for preparing gasoline by contacting a $C_4-$ fuel gas containing ethene and propene with a catalytic reformate containing $C_6$ to $C_8$ aromatic hydrocarbons over a zeolite catalyst. All of the above disclosures are incorporated herein by reference.

It has now been found that the amount of benzene in a gasoline product pool can be reduced by contacting a debutanized catalytic reformate feed with a fuel gas feed over a zeolite catalyst under olefins oligomerization and alkylation reaction conditions preferably in a fluidized bed reaction zone to obtain a product comprising alkylated aromatic hydrocarbons and oligomerized olefins, withdrawing the product from the fluidized bed reaction zone, and adding said product to a debutanizer column.

The $C_6$ to $C_8$ aromatics in the catalytic reformate can be converted to lower alkyl aromatic hydrocarbons while at the same time converting the $C_4-$ olefins to $C_5+$ hydrocarbons both of which products are suitable for use as gasoline blending stocks.

SUMMARY OF THE INVENTION

A continuous process is disclosed for providing an integrated product recovery system for a primary catalytic hydrocarbon reforming reactor and a secondary catalytic olefins oligomerization-alkylation reactor. The process comprises withdrawing reformer effluent from primary reformer reactor; separating in a primary separation zone the reformer effluent into a primary overhead stream comprising non-condensible $H_2$ and light paraffins and a primary bottoms stream comprising $C_6$ to $C_8$ aromatic hydrocarbons; withdrawing oligomerization effluent from secondary oligomerization-alkylation reactor; separating in a secondary separation zone the oligomerization effluent into a secondary overhead stream comprising non-condensible $C_4-$ hydrocarbons and inert gases and a secondary bottoms stream comprising $C_5+$ hydrocarbons; maintaining a fractionation column at a bottom temperature of about 127°–238° C. (260°–460° F.) and a pressure of about 687–1374 kPa (100–200 PSI); adding the primary bottoms stream and the secondary bottoms stream to the fractionation column; withdrawing from the top of the fractionation column a stream comprising $C_4-$ hydrocarbons; withdrawing from the bottom of the fractionation column a stream comprising $C_5+$ hydrocarbons; adding the $C_5+$ hydrocarbon stream to a reboiler unit; withdrawing from the reboiler unit a vapor stream comprising benzene and a liquid stream comprising $C_5+$ hydrocarbons boiling in the gasoline range; and adding at least a portion of said vapor stream comprising benzene to the secondary catalytic olefins oligomerization-alkylation reactor.

In an alternative embodiment, a liquid sidedraw comprising $C_5-C_8$ hydrocarbons can be withdrawn from the fractionation column at a point below where the non-condensible $C_4-$ hydrocarbons are withdrawn. This point is at a lowermost position of the upper section of the fractionation column and above the feed tray. The liquid sidedraw can be fed directly to the oligomerization-alkylation reactor for upgrading to gasoline blending stock.

In another alternative embodiment, a vapor sidedraw comprising $C_6-$ hydrocarbons can be withdrawn from the fractionation column at a point above where the condensible $C_5+$ hydrocarbons are withdrawn. Such a point is at an uppermost position of the lower section of the fractionation column. The vapor sidedraw can be fed directly to the oligomerization-alkylation reactor for upgrading to gasoline blending stock.

In all of the above embodiments, the fractionation system, comprising column 22 and reboiler 23 in FIG. 1 or column 22 and separator 28 FIG. 2, serves many functions. The fractionation system prepares the feed to the oligomerization-alkylation reactor, prepares the recycle stream for the oligomerization-alkylation reactor comprising unconverted light aromatics and stabilizes the gasoline-range hydrocarbons from said reactor.

One of the advantages of the present process and apparatus is that conversion of benzene to alkylated species can be maximized. Benzene can be recycled to the oligomerization-alkylation reactor to obtain high ratios. In a preferred embodiment, the wt./wt. ratio of benzene to olefins is about 3:1 to about 18:1.

In a preferred embodiment, the secondary catalytic olefins oligomerization-alkylation reactor is a turbulent fluidized bed reactor containing a catalyst comprising particulate zeolite having a silica: alumina molar ratio in the range from about 12:1 to 200:1, an apparent particle density of about 0.9 to 1.6 g/cm$^3$, and an average catalyst particle size of about 20 to 100 microns. Preferably, the light olefins feedstream added to the olefins oligomerization-alkylation reactor comprises a fuel gas obtained from a fluidized catalytic cracking (FCC) process. The wt./wt. ratio of benzene: olefins is about 2:1 to 20:1 in a combined feedstock to the catalytic olefins oligomerization-alkylation reactor, the combined feedstock comprising the light olefins feedstream and the fractionated light aromatic containing stream. Higher ratios of benzene to olefins require benzene recycle.

The present invention is directed to a process for the conversion of ethene and/or other light olefins-containing feedstocks and $C_6$ to $C_8$ aromatics containing feedstocks to heavier hydrocarbon products of higher octane value wherein the feedstocks are contacted at elevated temperature and pressure with a fixed, moving or fluidized bed of zeolite catalyst under conversion conditions.

In accordance with the present invention in the same reaction zone an ethene and/or other light olfins-rich stream can be upgraded to liquid hydrocarbons rich in olefinic gasoline and/or upgraded to lower alkyl aromatic hydrocarbons of higher octane value by catalytic conversion in a fixed, moving or fluidized bed of solid acid zeolite catalyst in a single pass or with recycle of light gas product.

The present invention is particularly useful for upgrading FCC light gas, which usually contains significant amounts of ethene or ethene and propene and for upgrading catalytic reformate which usually contains significant amounts of benzene, toluene, xylene and ethyl benzene.

OBJECTS OF THE INVENTION

It is an object of the present invention to provide an integrated refinery process for increasing the overall production of gasoline products.

It is another object of the present invention to reduce the overall fuel gas production and $C_6$ aromatic production of the refinery while at the same time increasing gasoline product octane.

It is a further object of the present invention to provide an economical process for catalytically converting a first hydrocarbon feed stream containing light olefins, including ethene and propene, and a second hydrocarbon stream containing $C_6$ to $C_8$ aromatic hydrocarbons, by contacting the two feed streams together over a fixed bed or fluidized bed of zeolite catalyst to convert the light olefin hydrocarbon feed to $C_5+$ hydrocarbon, e.g. $C_5+$ aliphatic hydrocarbon and/or to convert the aromatic hydrocarbons along with the light olefins to $C_7$ to $C_{11}$ aromatic hydrocarbon gasoline products.

It is a further object of the present invention to provide an integrated product recovery system for a primary catalytic hydrocarbon reforming reactor and a secondary catalytic olefins oligomerization-alkylation reactor. The use of a common benzene fractionation system for providing both fresh feed and recycle for the alkylation-oligomerization reactor allows for efficient recovery of a gasoline product from the integrated system.

DETAILED DESCRIPTION OF THE INVENTION

Figure 1:
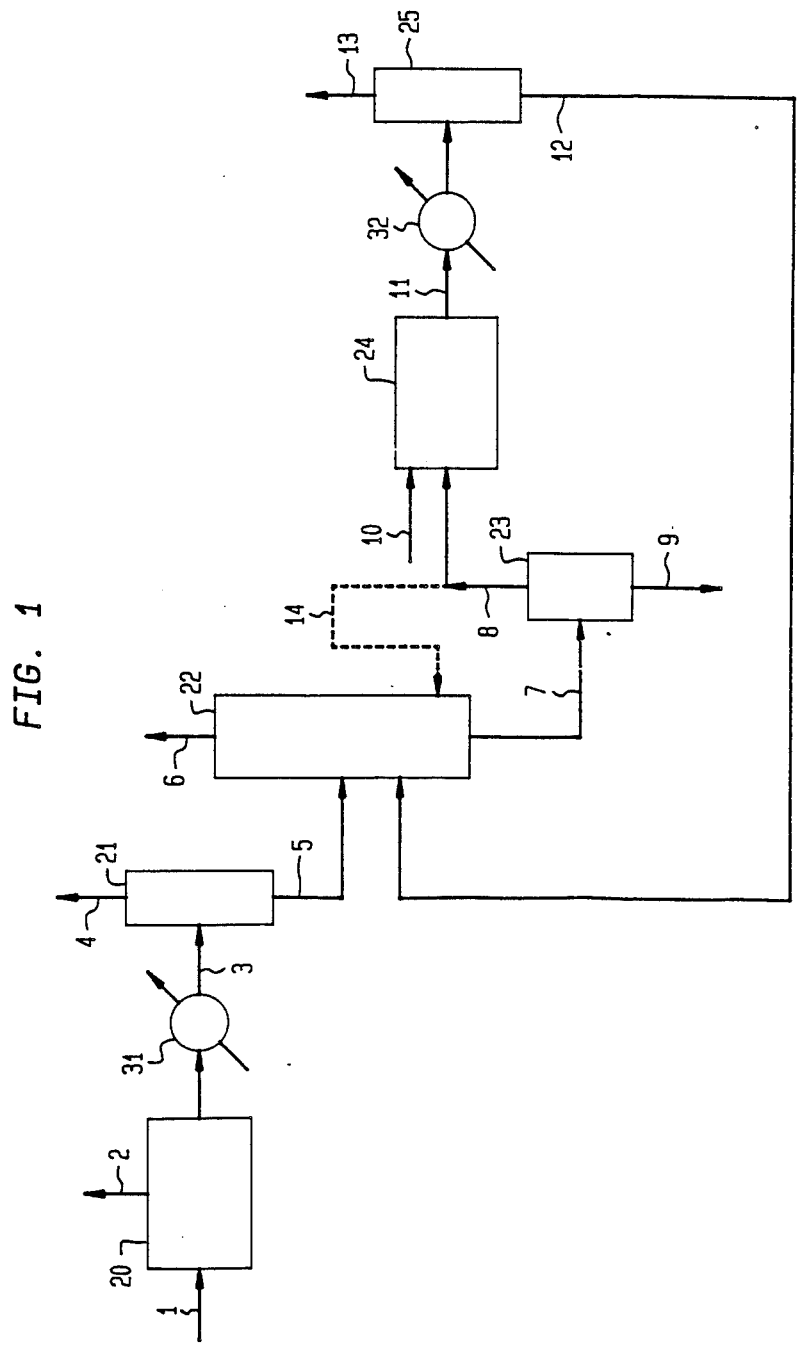
FIG. 1 is a flow diagram of the present process wherein a reboiler unit is employed to operatively connect debutanizer column with oligomerization reactor.

The present invention utilizes conventional petroleum refining steps including fractionation, hydrotreating, catalytic reforming and fluidized catalytic cracking and a zeolite catalyst process to upgrade the fuel gas and reformate process streams. A gasoline boiling range product is produced from the fuel gas stream or olefinic LPG stream from the fluidized catalytic cracking process step and the reformate stream from the catalytic reforming step.

In accordance with the present invention crude oil feed is subjected to atmospheric distillation to separate several hydrocarbon streams including a light gas, a gasoline boiling range naphtha, a middle distillate, a heavy distillate and a bottoms or reduced crude stream.

The naphtha stream is hydrotreated primarily to remove sulfur and nitrogen compounds and then fed to a catalytic reforming zone wherein the octane value of this stream is increased, the concentration of aromatic hydrocarbons is increased and hydrogen is produced as a by-product.

The middle distillate stream and heavy distillate stream are hydrotreated to produce products such as jet fuel and heating oil, respectively.

The reduced crude stream or a light fraction of said stream is fed to a fluidized catalytic cracking (FCC) zone in which there is produced a light gasoline boiling range stream, a light cycle oil, a fuel gas containing $C_1$ to $C_4$ olefins and paraffins and a heavy main column bottom stream.

The reduced crude may be fed into a vacuum fractionation column to produce vacuum gas oil and a resid fraction. Alternatively, reduced crude can be subjected to processing steps such as propane deasphalting, coking, etc.

The catalytic reformate from the reformer reaction section containing $C_6$ to $C_8$ aromatics is then fed to a debutanizer column, preferably after removal of light paraffinic hydrocarbons in a primary separation zone. The fuel gas stream containing $C_1$ to $C_4$ olefins and paraffins is fed to an olefins oligomerization-alkylation reactor preferably containing particulate zeolite catalyst. This same reactor also receives reformate after the reformate stream passes through the debutanizer column and a reboiler unit.

Alternatively, methanol, dimethylether (DME) or mixtures thereof can be added to the olefins oligomerization-alkylation reactor either in place of or together with light olefins feedstock to achieve the required per pass conversion. Methanol/DME mixtures are a good source of alkylating agent for aromatics such as benzene.

The zeolite catalyst reaction zone is operated under conditions such that ethene or ethene and propene in the fuel gas feed stream are converted to $C_5+$ olefinic gasoline product. The ethene or ethene and propene in the fuel gas feed stream also react with the $C_6$ to $C_8$ aromatic hydrocarbons in the reformate feed stream to produce $C_7$ to $C_{11}$ aromatic hydrocarbons such as toluene, xylene, ethylbenzene, methyl ethyl benzene, diethyl benzene, propyl benzene and methyl propyl benzene.

The effluent stream from the zeolite reaction zone is passed into a separator in which a $C_4-$ hydrocarbon stream is removed overhead. The bottoms from the separator contain $C_6$ to $C_{11}$ aromatic hydrocarbons and $C_5+$ hydrocarbons and is returned to debutanizer from which an overhead $C_4-$ gas stream is removed. Since benzene alkylation is not a complete reaction, uncoverted aromatics sent to the debutanizer will be partially separated utilizing the same equipment and recycled to the zeolite catalyst reaction zone. The debutanized gasoline product is removed as a bottoms product and is fed to the gasoline product pool after passing through a reboiler unit.

Recent developments in zeolite technology have provided a group of medium pore siliceous materials having similar pore geometry. Most prominent among these intermediate pore size zeolites is ZSM-5, which is usually synthesized with Bronsted acid active sites by incorporating a tetrahedrally coordinated metal, such as Al, Ga, B or Fe, within, the zeolitic framework. These medium pore zeolites are favored for acid catalysis; however, the advantages of ZSM-5 structures may be utilized by employing highly siliceous material or crystalline metallosilicate having one or more tetrahedral species having varying degrees of acidity. ZSM-5 crystalline structure is readily recognized by its X-ray diffraction pattern, which is described in U.S. Pat. No. 3,702,866 (Argauer, et al.), incorporated by reference.

The zeolite catalysts preferred for use herein include the medium pore (i.e., about 5-7A) shape-selective crystalline aluminosilicate zeolites having a silica-to-alumina ratio of at least 12, a constraint index of about 1 to 12 and acid cracking activity of about 1-200. In an operating reactor the coked catalyst may have an apparent activity (alpha value of about 1 to 80 under the process conditions to achieve the required degree of reaction severity. Representative of the ZSM-5 type zeolites are ZSM-5, ZSM-11, ZSM-12, ZSM-22, ZSM-23, and ZSM-35. ZSM-5 is disclosed in U.S. Pat. No. 3,702,886 and U.S. Pat. No. Re. 29,948. The ZSM-5 and ZSM-12 catalyst are preferred. Other suitable zeolites are disclosed in U.S. Pat. Nos. 3,709,979; 3,832,449; 4,076,979; 4,076,842; 4,016,245 and 4,046,839; 4,414,423; 4,417,086; 4,517,396 and 4,542,251. The disclosure of these patents are incorporated herein by reference. While suitable zeolites having a silica to coordinated metal oxide molar ratio of 12:1 to 200:1 or higher can be used, it is advantageous to employ a standard ZSM-5 having a silica: alumina molar ratio of about 25:1 to 70:1, suitably modified. A typical zeolite catalyst component having Bronsted acid sites may consist essentially of aluminosilicate ZSM-5 zeolite with 5 to 95 wt. % silica and/or alumina binder.

Certain of the ZSM-5 type medium pore shape selective catalysts are sometimes known as pentasils. In addition to the preferred aluminosilicates, the borosilicate, ferrosilicate and "silicalite" materials may be employed. It is advantageous to employ a standard ZSM-5 having a silica:alumina molar ratio of 25:1 to 70:1 with an apparent alpha value of 1-80 to convert 60 to 100 percent, preferably at least 70%, of the olefins in the feedstock and to convert 1 to 50% preferably at least 5% of the $C_6$-$C_8$ aromatics in the feedstock.

ZSM-5 type pentasil zeolites are particularly useful in the process because of their regenerability, long life and stability under the extreme conditions of operation. Usually the zeolite crystals have a crystal size from about 0.01 to over 2 microns or more, with 0.02-1 micron being preferred. The zeolite catalyst crystals are normally bound with a suitable inorganic oxide, such as silica, alumina, etc. to provide a zeolite concentration of about 5 to 95 wt. %. A preferred catalyst comprises 25% to 65% H-ZSM-5 catalyst contained within a silica-alumina matrix binder and having a fresh alpha value of less than 80. The process of the present invention can be carried out in a fixed bed, moving bed and fluidized bed reactor.

When employing a ZSM-5 type zeolite catalyst in fine powder form such a catalyst should comprise the zeolite suitably bound or impregnated on a suitable support with a solid density (weight of a representative individual particle divided by its apparent "outside" volume) in the range form 0.6-2 g/cc, preferably 0.9-1.6g/cc. The catalyst particles can be in a wide range of particle sizes up to about 250 microns, with an average particle size between 20 and 100 microns, preferably in the range of 10-150 microns and with the average particle size between 40 and 80 microns. These solid particles are placed in a fluidized reactor bed where the superficial fluid velocity is 0.2-2 meters per second. The velocity specified here is for an operation at a total reactor pressure of about 0 to 30 psig.

(100 to 300 kPa). Those skilled in the art will appreciate that at higher pressures, a lower gas velocity may be employed to ensure fluidized bed operation.

In the fluidized bed embodiment of the present invention it is advantageous to employ a particle size range consisting essentially of 1 to 150 microns. Average particle size is usually about 20 to 100 microns, preferably 40 to 80 microns. Particle distribution may be enhanced by having a mixture of larger and smaller particles within the operative range, and it is particularly desirable to have a significant amount of fines. Close control of distribution can be maintained to keep about 10 to 25 wt % of the total catalyst in the reaction zone in the size range less than 32 microns. This class of fluidizable particles is classified as Geldart Group A.

The light paraffin production and alkyl aromatic production is promoted by the zeolite catalysts having a high concentration of Bronsted acid reaction sites. Accordingly, an important criterion is selecting and maintaining the catalyst deactivation and regeneration rates to provide an apparent average steady state alpha value of about 1 to 50.

The preferred light olefin gas feedstock contains $C_2$ to $C_4$ alkenes (mono-olefins) including at least 2 mole % ethene, wherein the total $C_2$–$C_3$ alkenes are in the range of 10 to 40 wt %. Non-deleterious components, such as methane, $C_2$ to $C_4$ paraffins and inert gases, may be present. Some of the paraffins will be converted to $C_4+$ hydrocarbons depending on the reaction conditions and catalyst employed. A particularly useful feedstock is a light gas by-product of FCC gas oil cracking units containing typically 10–40 mol % $C_2$–$C_3$ olefins and 5–35 mol % $H_2$ with varying amounts of $C_1$ to $C_3$ paraffins and inert gas, such as $N_2$. The feedstock can contain primarily ethene or ethene and propene.

The catalytic reformate feedstock contains $C_6$ to $C_8$ aromatic hydrocarbons and optionally $C_5$ to $C_8$ paraffinic hydrocarbons. Though the catalytic reformate is a preferred feedstock, hydrocarbon process streams containing essentially the same hydrocarbon components can also be used.

In an alternative embodiment, the hydrocarbon process stream comprises effluent from dehydrocyclization reaction such as an "M-2 forming" process or a "cyclar" process. Effluent from an M-2 forming process as disclosed in U.S. Pats. No. 3,760,024 (Cattanach), incorporated herein by reference, comprises about 30 wt. % benzene and can thus be employed as a feedstock either in place of or together with reformate.

A process for decreasing the amount of benzene in effluent from a dehydrocyclization process is disclosed. The process comprises contacting a paraffinic feedstream with a shape-selective and zeolite catalyst under dehydrocyclization conditions in a primary dehydrocyclization reactor and withdrawing dehydrocyclization effluent from the reactor. The effluent is then separated in a primary separation zone into a primary overhead stream and a primary bottoms stream containing benzene. Oligomerization effluent is then withdrawn from a secondary oligomerization-alkylation reactor and separated in a secondary separation zone. From the secondary separation zone is withdrawn a secondary overhead stream comprising noncondensible $C_4-$ hydrocarbons and inert gases and a secondary bottoms stream comprising $C_5+$ hydrocarbons. The primary and secondary bottoms streams are added to a fractionation column which is maintained at a bottom temperature of about 127° C.–238° C. and a pressure of about 687 kPa –1374 kPa. An overhead stream comprising $C_4-$ hydrocarbons is withdrawn from the top of the fractionation column; and from the bottom of the column is withdrawn a stream comprising $C_5+$ hydrocarbons. The stream comprising $C_5+$ hydrocarbons is added to a reboiler unit. From the reboiler unit is withdrawn a vapor stream comprising benzene and a liquid stream comprising $C_5+$ gasoline boiling range hydrocarbons which can be recovered as product. The vapor stream is added to the olefins oligomerization-alkylation reactor. Also added to said reactor is an alkylating agent. The alkylating agent employed as a feedstream can be a light olefinic material such as ethene, propene or mixtures thereof; or an oxygenate such as methyl alcohol, dimethylether or mixtures thereof.

In the above description, the reboiler unit which receives the $C_5+$ hydrocarbons can be replaced with a splitter. The splitter receives the benzene-rich $C_5+$ hydrocarbons from the bottom of the fractionation column and fractionates said $C_5+$ hydrocarbons into a benzene-containing recycle stream and a substantially benzene-free gasoline product stream.

The contacting of the light olefin gas feed with debutanized catalytic reformate feed over the zeolite catalyst in the olefins oligomerization-alkylation reactor in accordance with the present invention produces the following products.

The ethene and propene components of the light olefin gas feed react to produce $C_5$ to $C_{10}$ olefinic, $C_5$ to $C_{10}$ paraffinic and $C_6$ to $C_{10}$ aromatic gasoline products which have a higher product value than the ethene and propene in the feed. Depending on operating conditions and ratio of aromatics to olefins in the oligomerization-alkylation reactor, olefins oligomerization varies.

The ethene and propene components of the light olefin gas feed in addition react with the $C_6$ to $C_8$ aromatics in the catalytic reformate feed to produce primarily $C_7$ to $C_{11}$ aromatics which may themselves rearrange and transalkylate over the zeolite catalyst.

The $C_7$ to $C_{11}$ aromatic hydrocarbon product obtained includes $C_1$ to $C_4$ lower alkyl substituted aromatic hydrocarbons such as methyl, ethyl, propyl and butyl benzene compounds. The $C_7$ to $C_{11}$ aromatic hydrocarbon product containing one or more of the foregoing lower alkyl substituents does not exceed 5. Typical $C_7$ to $C_{11}$ aromatic hydrocarbons include toluene, ethyl benzene, xylene, methylethyl benzene, propyl benzene, methyl-propyl and butyl benzene compounds. The $C_7$ to $C_{11}$ aromatic hydrocarbons include toluene, ethyl benzene, methyl-ethyl benzene, propyl benzene, methyl-propyl benzene, trimethyl benzene, durene, butyl benzene, methyl-butyl benzene and diethyl benzene.

The incorporation of the $C_5+$ hydrocarbon component, e.g. the $C_5+$ olefinic hydrocarbons, into the $C_7$–$C_{11}$ aromatic hydrocarbon component enriches the overall octane quality of the gasoline product obtained.

The zeolite catalyst process conditions of temperature and pressure are closely controlled to minimize cracking of paraffinic hydrocarbons in the feed and is an important feature of the present invention.

Unreacted ethene, propene, and butene, in addition to unreacted light aromatics can be recycled to the zeolite catalyst reactor.

The ethene and propene in the light olefin feed are converted in an amount of 60 to 100, preferably 80 to 100 and more preferably 80 to 95 wt. % of the feed.

The $C_6$ to $C_8$ aromatics in the catalytic reformate feed, including benzene, toluene and $C_8$ aromatics, are converted in an amount of 5 to 60 and preferably 25 to 50 wt. % per pass.

The olefins oligomerization-alkylation reaction employing a ZSM-5 type zeolite catalyst is carried out at temperatures of 400° to 800° F. (204° to 427° C.) for example 500° to 800° F. (260° to 427° C.), preferably 500° to 750° F. (260° to 399° C.) and more preferably 600° to 750° F. (316° to 399° C.).

The pressure at which the reaction is carried out is an important parameter of the invention. The process can be carried out at pressures of 3 to 300 psig (121 to 2161 kPa) preferably 100 to 400 psig (790 to 2860 kPa) and more preferably 150–300 psig (1131 to 2161 kPa).

The weight hourly space velocity (WHSV) of the light olefin feed and the debutanized catalytic reformate feed are also important parameters of the process.

The principal reactants in the process are the ethene, propene, and/or butene constituents of the light olefin gas and the $C_6$ to $C_8$ aromatic constituent of the catalytic reformate, and the WHSV are given in terms of these components.

The total $C_4-$ olefins ethene and propene WHSV can be 0.1 to 10, preferably 0.5 to 3 and more preferably 0.5 to 1.5.

The $C_6$ to $C_8$ aromatics WHSV can be 0.01 to 6.0, preferably 0.1 to 2.0 and more preferably 0.1 to 0.5.

The process can be carried out in a conventional fixed bed, moving bed, riser, or fluidized bed reactor.

The reactor can assume any technically feasible configuration, but several important criteria should be considered. The bed of catalyst in a fluid bed reactor can be about 5-20 meters in height. Fine particles may be included in the bed, especially due to attrition, and the fines may be entrained in the product gas stream. A typical reactor unit employs a temperature-controlled catalyst zone with gas or liquid feed quench, whereby the reaction temperature can be carefully controlled in the desired operating range of about 400° F. to 800° F. (204° C. to 427° C.), preferably at average reactor temperature of 500° F. to 750° F. (260° C. to 399° C.) and more preferably at an average reaction temperature of 600° F. to 750° F. (316° C. to 399° C.). The reaction temperature may be in part controlled by exchanging hot reactor effluent with feedstock and/or recycle streams. Optional heat exchangers may recover heat from the effluent stream prior to fractionation. Part or all of the reaction heat can be removed from the reactor by using cold feed, whereby reactor temperature can be controlled by adjusting feed temperature.

A continuous process is disclosed for decreasing the amount of benzene in gasoline pool. The process comprises contacting hydrocarbon effluent from a catalytic hydrotreating reactor with catalyst in a reforming reactor to obtain a reformate stream; withdrawing reformate stream and adding said stream to a primary separation zone; withdrawing from the primary separation zone a primary bottoms stream comprising $C_6$ to $C_8$ aromatic hydrocarbons rich in benzene; contacting a fuel gas obtained from a fluidized catalytic cracking reactor with a zeolite catalyst in an olefins oligomerization-alkylation reactor to obtain a gasoline rich hydrocarbon stream; withdrawing the gasoline rich stream and adding said stream to a secondary separation zone; withdrawing from the secondary separation zone a secondary bottoms stream comprising $C_5+$ hydrocarbons; maintaining a debutanizer column at a bottom temperature of about 260° F.-460° F. (127°-238° C.) and a pressure of about 100-200 psi (687-1374 kPa); adding the primary bottoms stream to an intermediate level of the debutanizer column; adding the secondary bottoms stream to the debutanizer column; withdrawing from the debutanizer column a stream comprising $C_5+$ hydrocarbons; adding the $C_5+$ hydrocarbons stream to a tertiary separation column; withdrawing from said tertiary column a tertiary overhead stream comprising $C_6-$ hydrocarbons, a tertiary bottoms stream comprising $C_7+$ hydrocarbons boiling in the gasoline range, and a tertiary intermediate stream comprising $C_6+$ aromatic hydrocarbons rich in benzene; and adding at least a portion of said intermediate stream rich in benzene to the olefins oligomerization-alkylation reactor, whereby benzene is alkylated to produce $C_1$ to $C_4$ lower alkyl mono-substituted, di-substituted and poly-substituted aromatic hydrocarbons.

In a preferred embodiment, the zeolite catalyst in the olefins oligomerization-alkylation reactor comprises particulate zeolite having a silica: alumina molar ratio in the range form about 12:1 to 200:1, an apparent particle density of about 0.9 to 1.6 g/cm$^3$, an average catalyst particle size of about 20 to 100 microns. The wt./wt. ratio of benzene: olefins is about 2:1 to 20:1 in a combined feedstock of the olefins oligomerization-alkylation reactor, the combined feedstock comprising fuel gas from a fluidized catalytic cracking reactor and the intermediate stream rich in benzene from the tertiary separation column. Preferably, the bottoms stream withdrawn from tertiary column comprising $C_7+$ hydrocarbons boiling in the gasoline range is recovered as product.

In a process for the production of gasoline which comprises contacting a fuel gas from a fluid catalytic cracking process, said fuel gas comprising $C_4-$ hydrocarbons including ethene and propene, with a catalytic reformate feed stream comprising $C_6$ to $C_8$ aromatic hydrocarbons over a zeolite catalyst to obtain gasoline boiling range hydrocarbon product, the improvement of the present process comprises maintaining a fractionation column at a bottom temperature of about 260° F.-460° F. (127° C.-238° C.) and a pressure of about 100-200 psi (687-1374 kPa); adding to the fractionation column a reformate stream comprising $C_6$ to $C_8$ aromatic hydrocarbons; withdrawing from the top of the fractionation column an overhead stream comprising $C_4-$ hydrocarbons; withdrawing from the bottom of the fractionation column a lower stream comprising $C_5+$ hydrocarbons; adding said lower stream to a reboiler unit; withdrawing from reboiler unit a first stream comprising gasoline boiling range hydrocarbon product; withdrawing from said reboiler a second stream comprising benzene; adding at least a portion of said second stream to an olefins oligomerization-akylation reactor containing crystalline aluminosilicate catalyst particles; adding fuel gas comprising $C_4-$ hydrocarbons including ethene and propene to said olefins oligomerization-alkylation reactor; withdrawing from the oligomerization-alkylation reactor an effluent comprising $C_7$ to $C_{11}$ aromatic hydrocarbons and hydrocarbon oligomers; and adding said effluent to the fractionation column. The first stream withdrawn from reboiler and comprising gasoline boiling range hydrocarbons is recovered as product and a portion of the second stream withdrawn from the reboiler and comprising $C_6$ to $C_8$ aromatic hydrocarbons is returned to the fractionation column. The olefins oligomerization-alkylation reactor is a turbulent fluidized bed reactor and the crystalline aluminosilicate catalyst particles comprise a zeolite having a silica: alumina molar ratio in the range from about 20:1 to 200:1, an apparent particle density of about 0.9 to 1.6 g/cm$^3$, and an average catalyst particle size of about 20 to 100 microns. In a preferred embodiment, the zeolite has the structure of ZSM-5.

An apparatus is disclosed for providing an integrated product recovery system for a catalytic hydrocarbon reforming reactor or dehydrocyclization reactor and a catalytic olefins oligomerization-alkylation reactor. The apparatus comprises a debutanizer column comprising a primary inlet for a reformer effluent from a reforming reactor or dehydrocyclization effluent from a dehydrocyclization reactor, a secondary inlet for an alkylated oligomerized effluent from an olefins oligomerization-alkylation reactor, an overhead outlet for a stream comprising unstabilized $C_4-$ hydrocarbons, and a bottoms outlet for a liquid stream comprising unstabilized $C_5+$ aliphatic and aromatic hydrocarbons; and a receiving unit operatively connected to the debutanizer column, the receiving unit comprising a means for transporting the bottom liquid stream from the debutanizer to the receiving unit, an upper outlet for $C_6+$ hydrocarbons rich in benzene and a lower outlet for $C_7+$ hydrocarbons boiling in the gasoline range. The receiving unit comprises a reboiler unit or a separation column. Preferably, the apparatus even further comprises an olefins oligomerization-alkylation turbulent regime fluidized bed reactor containing siliceous metallosilicate acid zeolite particles having the structure of ZSM-5 zeolite and a silica: alumina molar ratio of about 12:1 to 70:1, means for passing the $C_6+$ hydrocarbons rich in benzene from the upper outlet of the receiving unit to the olefins oligomerization-alkylation reactor, a means for adding to the oligomerization-alkylation reactor a feedstock comprising $C_2+$ lower olefins, a means for withdrawing from the oligomerization-alkylation reactor a hydrocarbon effluent comprising $C_7$ to $C_{11}$ aromatic hydrocarbons and hydrocarbon oligomers and a means for adding said unstabilized $C_5+$ hydrocarbon effluent to the debutanizer column.

Referring to FIG. 1, a hydrotreated hydrocarbon feedstock 1 enters a catalytic reforming zone 20 wherein the octane value of the feedstock is increased, the concentration of aromatic hydrocarbons is increased and hydrogen is produced as a by-product. The hydrotreated feedstock is normally obtained from a gasoline boiling range naphtha Hydrogen gas is withdrawn from reformer 20 as by line 2.

A catalytic reformate containing $C_6$ to $C_8$ aromatic hydrocarbons and paraffins is withdrawn from reforming zone 20 as by line 3, cooled in condenser 31 and added to a separation drum 21. An overhead stream comprising paraffinic hydrocarbons is withdrawn via line 4, a bottoms stream comprising $C_6$ to $C_8$ aromatic hydrocarbons is withdrawn via line 5 and enters debutanizer column 22. The debutanizer or fractionation column 22 is maintained at a bottom temperature of about 260° F.–460° F. (127° C.–238° C.) and a pressure of about 100–200 psi (687–1374 kPa). The debutanizer accepts not only the reformate stream, as described above, but also a stream withdrawn from an olefins oligomerization-alkylation reaction zone via line 12.

An overhead stream comprising $C_4-$ hydrocarbons is withdrawn from the debutanizer column 22 as by line 6. This stream can be further processed to recover valuable components such as n-butane and iso-butane.

A bottoms stream comprising $C_5+$ hydrocarbons and rich in benzene is withdrawn from the debutanizer column 22 via line 7 and enters a reboiler unit 23. A product comprising gasoline boiling range ($C_5$–$C_{10}$) hydrocarbons is withdrawn from reboiler 23 via line 9. The product can be sent directly to gasoline pool for further processing.

An intermediate stream rich in benzene is withdrawn from reboiler 23 as by line 8 and enters fluidized bed olefins oligomerization-alkylation reactor 24. In an alternative embodiment, a portion of the benzene-rich stream is returned to debutanizer column 22 as by line 14.

The benzene-rich stream is one feed to the oligomerization-alkylation reactor 24. A second feed comprising $C_2+$ olefinic hydrocarbons enters oligomerization-alkylation reactor 24 as by line 10. This second feed is preferably an FCC fuel gas steam obtained by treating vacuum gas oil or resid in a fluidized catalytic cracking (FCC) zone. Other products obtained from the FCC operation are a light gasoline, distillate and 700° F. hydrocarbon boiling range material. The fuel gas contains typically 10–40 mol % $C_2$–$C_4$ olefins and 5–35 mol % $H_2$ with varying amounts of $C_1$–$C_3$ paraffins and inert gas, such as $N_2$.

It is within the scope of the present invention to send any olefin-containing feedstock as by line 10 to oligomerization-alkylation zone 24. The feedstock can be ethene, propene, butenes or mixtures thereof. Alternatively, the feed can be methanol, dimethylether or mixtures thereof.

A stream comprising oligomers and di- and polyalkylated aromatic hydrocarbons is withdrawn from oligomerization-alkylation reactor 24 as by line 11, cooled in condenser 32 and added to secondary separation zone 25.

A secondary overhead stream is withdrawn form separator 25 as by line 13. The secondary overhead contains $C_4-$ hydrocarbons and inert gases. A secondary bottoms stream comprises $C_5+$ hydrocarbons including the unreacted feed, hydrocarbons boiling in the gasoline range and aromatic hydrocarbons such as toluene, xylene, ethyl benzene, methylethyl benzene and the like. The secondary bottoms stream is withdrawn from separator 25 as by line 12 and added to debutanizer column 22. In a preferred embodiment, the secondary bottoms stream is added to the debutanizer 22 at a point below the added reformate stream.

Figure 2:
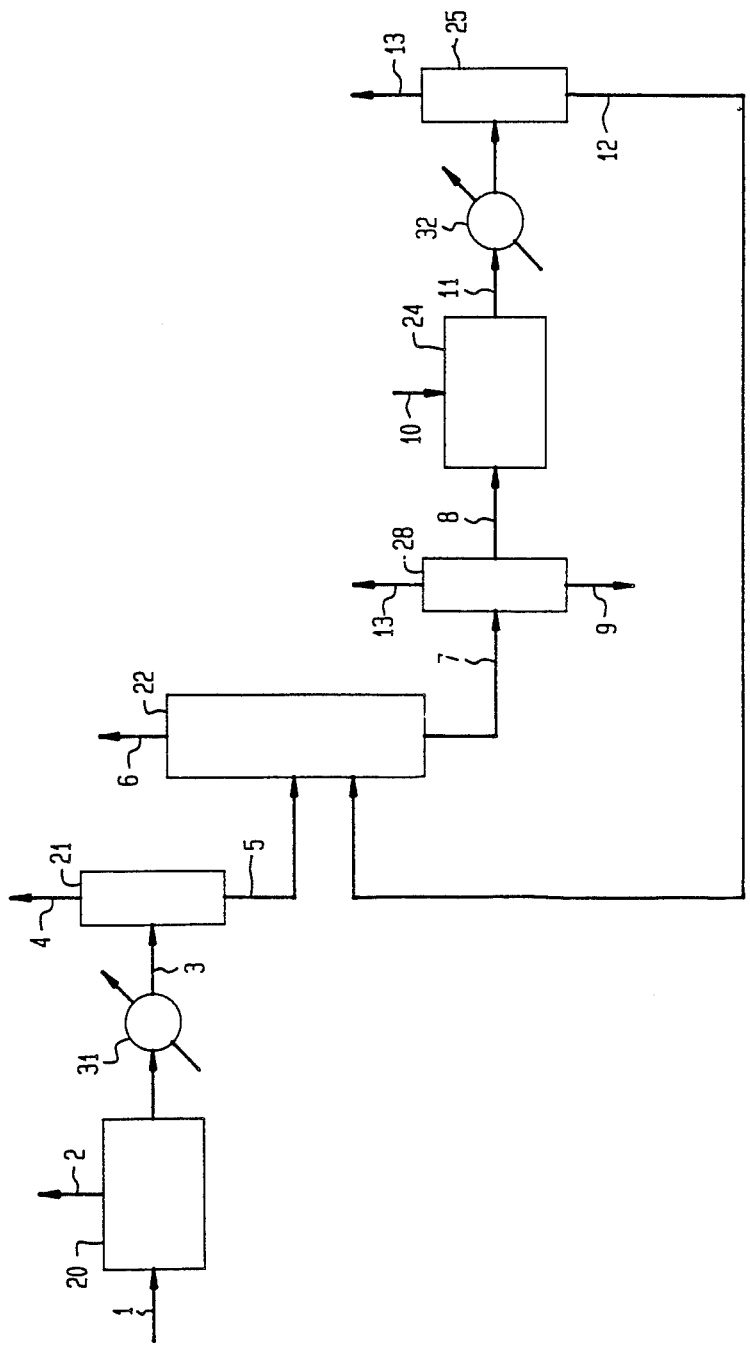
FIG. 2 is a flow diagram of the present process wherein a tertiary separation unit is employed to operatively connect debutanizer column with oligomerization reactor.

FIG. 2 is a diagram of an alternative embodiment of the present process. Refer to the description of FIG. 1 for an explanation of the reactant and product flowpath and the various process equipment. The point of difference in FIG. 2 is the use of a tertiary separation column 28. A debutanized stream comprising $C_6$ to $C_8$ aromatic hydrocarbons is withdrawn from debutanizer column 22 as by line 7 and enters tertiary separation zone 28. A tertiary overhead stream comprising $C_6-$ hydrocarbons is withdrawn as by line 13. A tertiary bottoms stream comprising $C_7+$ hydrocarbons is withdrawn via line 9. An intermediate steam comprising benzene is withdrawn from tertiary separation zone 28 via line 8 and enters olefins oligomerization-alkylation reactor 24. As in FIG. 1, an olefins-containing stream is also added to oligomerization-alkylation reactor 24 as by line 10. Effluent is withdrawn from reactor 24 as by line 11 and further processed as described in FIG. 1 above.

Unconverted aromatics are separated and recycled for upgrading by the present process. Another advantage of the process is that the unstabilized gasoline withdrawn from the oligomerization-alkylation reactor is stabilized in the disclosed fractionation system.

For purposes of clarity in the above description of the invention various subsystems and apparatus normally associated with the operation of the process have not been shown. The omitted items include pump, temperature, pressure and flow control systems, reactor and fractionator internals, crude column strippers, separators, absorbers, reboilers, overhead condensing systems, etc. which may be of conventional design.

While the invention has been shown by describing preferred embodiments of the process, there is no intent to limit the inventive concept, except as set forth in the following claims.

We claim:

1. A continuous process for providing an integrated product recovery system for a primary catalytic hydrocarbon reforming reactor and a secondary catalytic olefins oligomerization-alkylation reactor, the process comprising:
   withdrawing reformer effluent from primary reformer reactor;
   separating in a primary separation zone the reformer effluent into a primary overhead stream comprising noncondensible light paraffins and a primary bottoms stream comprising $C_6$ to $C_8$ aromatic hydrocarbons;
   withdrawing oligomerization effluent from secondary oligomerization-alkylation reactor;
   separating in a secondary separation zone the oligomerization effluent into a secondary overhead stream comprising $C_4-$ hydrocarbons and inert gases and a secondary bottoms stream comprising $C_5+$ hydrocarbons;
   maintaining a fractionation system comprising a fractionation column at a bottom temperature of about 127° C.-238° C. and a pressure of about 687-1374 kPa, and a reboiler unit;
   adding the primary bottoms stream and the secondary bottoms stream to the fractionation column;
   withdrawing from the top of the fractionation column a stream comprising $C_4-$ hydrocarbons;
   withdrawing from the bottom of the fractionation column a stream comprising $C_5+$ hydrocarbons;
   adding the $C_5+$ hydrocarbon stream to the reboiler unit;
   withdrawing from the reboiler unit a vapor stream comprising benzene and a liquid stream comprising $C_5+$ hydrocarbons boiling in the gasoline range;
   adding at least a portion of said vapor stream comprising benzene to the secondary catalytic olefins oligomerization-alkylation reactor; and
   adding a light olefins feedstream comprising ethene, propene or mixtures thereof to the olefins oligomerization-alkylation reactor.

2. A process according to claim 1 wherein the secondary bottoms stream is added to the fractionation column at a point below the addition of the primary bottoms stream to said column.

3. A process according to claim 1 wherein the liquid stream withdrawn from reboiler and comprising $C_5+$ hydrocarbons boiling in the gasoline range is recovered as product.

4. A process according to claim 1 wherein the light olefins feedstream added to the olefins oligomerization-alkylation reactor comprises a fuel gas obtained from a fluidized catalytic cracking (FCC) process.

5. A process according to claim 1 wherein the secondary catalytic olefins oligomerization-alkylation reactor comprises a turbulent fluidized bed reactor containing a catalyst comprising particulate zeolite having a silica: alumina molar ratio in the range from about 12:1 to 200:1, an apparent particle density of about 0.9 to 1.6 g/cm$^3$, and an average catalyst particle size of about 20 to 100 microns.

6. A process according to claim 5 wherein the zeolite comprises a siliceous metallosilicate acid zeolite having the structure of ZSM-5 and a silica:alumina molar ratio of about 25:1 to 70:1.

7. A process according to claim 1 wherein the wt./wt. ratio of benzene: olefins is about 2:1 to 20:1 in a combined feedstock to the catalytic olefins oligomerization-alkylation reactor, the combined feedstock comprising the light olefins feedstream and the vapor stream from the reboiler unit.

8. A process according to claim 1 further comprising adding an alkylating agent comprising methanol, dimethylether or mixtures thereof as feedstream to the olefins oligomerization-alkylation reactor.

9. A continuous process for decreasing the amount of benzene in gasoline pool comprising:
   contacting hydrocarbon effluent from a catalytic hydrotreating reactor with catalyst in a reforming reactor to obtain a reformate stream;
   withdrawing reformate stream and adding said stream to a primary separation zone;
   withdrawing from the primary separation zone a primary bottoms stream comprising $C_6$ to $C_8$ aromatic hydrocarbons rich in benzene;
   contacting a fuel gas obtained from a fluidized catalytic cracking reactor with a zeolite catalyst in an olefins oligomerization-alkylation reactor to obtain a gasoline rich hydrocarbon stream;
   withdrawing oligomerized stream and adding said stream to a secondary separation zone;
   withdrawing from the secondary separation zone a secondary bottoms stream comprising $C_5+$ hydrocarbons;
   maintaining a fractionation system comprising a debutanizer column at a bottom temperature of about 127° C. to 238° C. and a pressure of about 687 to 1374 kPa; and a tertiary separation column;
   adding the primary bottom stream to an intermediate level of the debutanizer column;
   adding the secondary bottoms stream to the debutanizer column;
   withdrawing from the debutanizer column a stream comprising $C_5+$ hydrocarbons;
   adding the $C_5+$ hydrocarbon stream to a tertiary separation column;
   withdrawing from said tertiary column a tertiary overhead stream comprising $C_6-$ hydrocarbons, a tertiary bottoms stream comprising $C_7+$ hydrocarbons boiling in the gasoline range, and a tertiary intermediate stream comprising benzene; and
   adding at least a portion of said intermediate stream comprising benzene to the olefins oligomerization-alkylation reactor, whereby benzene is alkylated to produce $C_1$ to $C_4$ lower alkyl mono-substituted, di-substituted and poly-substituted aromatic hydrocarbons.

10. A process according to claim 9 wherein the bottoms stream withdrawn from tertiary column comprising $C_7+$ hydrocarbons boiling in the gasoline range is recovered as product.

11. A process according to claim 9 wherein the zeolite catalyst in the olefins oligomerization-alkylation reactor comprises particulate zeolite having a silica: alumina molar ratio in the range from about 12:1 to 200:1, an apparent particle density of about 0.9 to 1.6 g/cm$^3$, an average catalyst particle size of about 20 to 100 microns.

12. A process according to claim 9 wherein the wt./wt. ratio of benzene: olefins is about 2:1 to 20:1 in a combined feedstock to the olefins oligomerization-alkylation reactor, the combined feedstock comprising fuel gas from a fluidized catalytic cracking reactor and the intermediate stream rich in benzene from the tertiary separation column.

13. In a process for the production of gasoline which comprises contacting a fuel gas from a fluid catalytic cracking process, said fuel gas comprising $C_4-$ hydrocarbons including ethene and propene, with a catalytic reformate feed stream comprising $C_6$ to $C_8$ aromatic hydrocarbons over a zeolite catalyst to obtain gasoline boiling range hydrocarbon product, the improvement comprising:

maintaining a fractionation column at a bottom temperature of about 127° C.–238° C. and a pressure of about 687–1374 kPa;

adding to the fractionation column a reformate stream comprising $C_6$ to $C_8$ aromatic hydrocarbons;

withdrawing from the top of the fractionation column an overhead stream comprising $C_4-$ hydrocarbons;

withdrawing from the bottom of the fractionation column a lower stream comprising $C_5+$ hydrocarbons;

adding said lower stream to a reboiler unit;

withdrawing from reboiler unit a first stream comprising gasoline boiling range hydrocarbon product;

withdrawing from said reboiler a second stream comprising benzene;

adding at least a portion of said second stream to an olefins oligomerization-alkylation reactor containing crystalline aluminosilicate catalyst particles;

adding fuel gas comprising $C_4-$ hydrocarbons including ethene and propene to said olefins oligomerization-alkylation reactor;

withdrawing from the oligomerization-alkylation reactor an effluent comprising $C_7$ to $C_{11}$ aromatic hydrocarbons and hydrocarbon oligomers; and adding said effluent to the fractionation column.

14. A process according to claim 13 wherein the oligomerization reactor effluent stream is added to the fractionation column at a point below the addition of the reformate stream to said column.

15. A process according to claim 13 wherein the first stream withdrawn from reboiler and comprising gasoline boiling range hydrocarbons is recovered as product and a portion of the second stream withdrawn from the reboiler and comprising benzene is returned to the fractionation column.

16. A process according to claim 13 wherein the olefins oligomerization-alkylation reactor is a turbulent fluidized bed reactor and the crystalline aluminosilicate catalyst particles comprise a zeolite having a silica:alumina molar ratio in the range form about 12:1 to 200:1, an apparent particle density of about 0.9 to 1.6 g/cm$^3$, and an average catalyst particle size of about 20 to 100 microns.

17. A process according to claim 16 wherein the zeolite has the structure of ZSM-5.

18. A continuous process for upgrading benzene-containing hydrocarbon stream comprising:

contacting a paraffinic feedstream with a shape-selective acid zeolite catalyst under dehydrocyclization conditions in a primary reactor;

withdrawing dehydrocyclization effluent from said reactor;

adding effluent to a primary separation zone;

separating said effluent into a primary overhead stream and a primary bottoms stream containing benzene;

withdrawing oligomerization effluent from a secondary oligomerization-alkylation reactor;

adding oligomerization effluent to a secondary separation zone;

separating said effluent into a secondary overhead stream comprising $C_4-$ hydrocarbons and inert gases and a secondary bottoms stream comprising $C_5+$ hydrocarbons;

adding the primary bottoms stream and the secondary bottoms stream to a fractionation column maintained at a bottom temperature of about 127° C.–238° C. and a pressure of about 687 kPa–1374 kPa;

withdrawing from said fractionation column an overhead stream comprising $C_4-$ hydrocarbons and a bottoms stream comprising $C_5+$ hydrocarbons;

adding the bottoms stream comprising $C_5+$ hydrocarbons to a reboiler unit;

withdrawing from the reboiler unit a vapor stream comprising benzene and a liquid stream comprising $C_5+$ gasoline boiling range hydrocarbons;

adding said vapor stream to the oligomerization-alkylation reactor; and adding an alkylating agent as feedstream to said oligomerization-alkylation reactor.

19. A process according to claim 18 wherein the liquid stream comprising $C_5+$ gasoline boiling range hydrocarbons is recovered as product.

20. A process according to claim 18 wherein the shape-selective acid zeolite catalyst comprises ZSM-5.

21. A process according to claim 18 wherein the alkylating agent comprises methanol, dimethylether or mixtures thereof.

22. A process according to claim 18 wherein a splitter is employed in place of the reboiler unit.

* * * * *